| (12) United States Patent<br>Bindayel | (10) Patent No.: US 9,980,787 B2<br>(45) Date of Patent: May 29, 2018 |
|---|---|

(54) ORTHODONTIC SYSTEMS

(71) Applicant: Naif Bindayel, Riyadh (SA)

(72) Inventor: Naif Bindayel, Riyadh (SA)

( * ) Notice: Subject to any disclaimer, the term of this patent is extended or adjusted under 35 U.S.C. 154(b) by 0 days. days.

(21) Appl. No.: 15/160,255

(22) Filed: May 20, 2016

(65) Prior Publication Data

US 2017/0128164 A1 May 11, 2017

Related U.S. Application Data

(60) Provisional application No. 62/252,760, filed on Nov. 9, 2015.

(51) Int. Cl.
| A61C 3/00 | (2006.01) |
| A61B 90/98 | (2016.01) |
| A61C 7/20 | (2006.01) |
| A61C 7/00 | (2006.01) |
| A61C 7/12 | (2006.01) |
| A61C 7/14 | (2006.01) |
| A61C 7/22 | (2006.01) |
| A61C 7/28 | (2006.01) |
| A61B 90/00 | (2016.01) |

(52) U.S. Cl.
CPC ........... *A61B 90/98* (2016.02); *A61C 7/002* (2013.01); *A61C 7/12* (2013.01); *A61C 7/14* (2013.01); *A61C 7/20* (2013.01); *A61C 7/22* (2013.01); *A61C 7/28* (2013.01); *A61B 2090/064* (2016.02); *A61B 2560/0219* (2013.01); *A61B 2560/045* (2013.01)

(58) Field of Classification Search
CPC .. A61C 1/003; A61C 1/04; A61C 1/06; A61C 7/285; A61C 7/20; A61C 7/22; A61C 7/28; A61C 7/12; A61C 7/002; A61C 7/14; A61B 90/98; A61B 2090/064; A61B 2560/0219; A61B 2560/045
USPC ................................. 433/8–18, 20
See application file for complete search history.

(56) References Cited

U.S. PATENT DOCUMENTS

| 4,292,025 A | 9/1981 | Förster | |
| 5,032,080 A * | 7/1991 | Hakansson | .............. A61C 7/16<br>433/8 |

(Continued)

OTHER PUBLICATIONS

International Search Report and Written Opinion of the International Searching Authority for International Application No. PCT/IB2016/056759 dated Apr. 4, 2017.

(Continued)

*Primary Examiner* — Heidi M Eide (74) *Attorney, Agent, or Firm* — Fish & Richardson P.C.

(57) ABSTRACT

An orthodontic system includes an orthodontic arch wire having a shape that corresponds to a dental arch, the arch wire having a first end portion that has a first series of grooves. In some examples, the first end portion has a second series of grooves, and the first and second series of grooves are positioned on opposite sides of the first end portion. In some examples, a bracket can be provided in which the bracket has a first gear and a second gear, the first gear is configured to engage the first series of grooves and the second gear is configured to engage the second series of grooves, enabling one or both of the first and second gears to drive the first end portion and provide a force along a longitudinal direction of the arch wire.

29 Claims, 10 Drawing Sheets

(56) References Cited

U.S. PATENT DOCUMENTS

| | | | |
|---|---|---|---|
| 5,035,614 A * | 7/1991 | Greenfield | A61C 7/12 433/18 |
| 5,954,502 A | 9/1999 | Tuenge et al. | |
| 6,632,088 B2 * | 10/2003 | Voudouris | A61C 7/12 433/18 |
| 7,306,458 B1 | 12/2007 | Lu | |
| 7,581,714 B2 * | 9/2009 | Machu | B66F 3/02 254/100 |
| 9,531,237 B2 | 12/2016 | Miller | |
| 2001/0029008 A1 | 10/2001 | Jordan et al. | |
| 2003/0031975 A1 | 2/2003 | Voudouris | |
| 2003/0152889 A1 | 8/2003 | Uji | |
| 2005/0269821 A1 | 12/2005 | Nadel et al. | |
| 2006/0074431 A1 | 4/2006 | Sutton et al. | |
| 2007/0184399 A1 | 8/2007 | Salich | |
| 2008/0248439 A1 * | 10/2008 | Griffith | A61C 7/12 433/8 |
| 2009/0286195 A1 | 11/2009 | Sears et al. | |
| 2009/0317757 A1 | 12/2009 | Lemchen | |
| 2012/0148973 A1 | 6/2012 | Johnston | |
| 2014/0134562 A1 | 5/2014 | Wu et al. | |
| 2015/0305833 A1 | 10/2015 | Cosse | |

OTHER PUBLICATIONS

Non-Final Office Action for U.S. Appl. No. 15/160,234 dated Apr. 10, 2017.
Non-Final Office Action for U.S. Appl. No. 15/160,291 dated Apr. 7, 2017.

* cited by examiner

ORTHODONTIC SYSTEMS

CROSS-REFERENCE TO RELATED APPLICATIONS

This application claims priority to U.S. Provisional Patent Application 62/252,760, filed on Nov. 9, 2015. This application is related to U.S. patent application Ser. No. 15/160,275, filed on May 20, 2016, Ser. No. 15/160,234, filed on May 20, 2016, Ser. No. 15/160,291, filed on May 20, 2016, Ser. No. 15/160,277, filed on May 20, 2016, and Ser. No. 15/160,337, filed on May 20, 2016. The contents of the above applications are incorporated by reference in their entirety.

TECHNICAL FIELD

This disclosure relates to orthodontic systems.

BACKGROUND

Orthodontic braces are useful in correcting alignment of teeth to proper positions and orientations in the dental arch and to improve dental health. In some examples, orthodontic braces include metal brackets bonded to the teeth and arch wires that are tied to the brackets by elastic ties. The arch wires are designed to apply force to the brackets and teeth, causing the teeth to slowly move or rotate in prescribed directions. The arch wires are adjusted, e.g., every three or four weeks during treatment to maintain pressure in order to supply prescribed forces to the teeth. There are many types of dental braces. For example, braces can be self-ligating such that the arch wire clips into the brackets without the need for ligatures. Some dental braces use computer-adjusted wires. These braces use the same principle of force delivery by an external source outside of the bracket (e.g., wire, coils, or elastics). In some examples, a bracket may have a base that is angulated to combine torque, angulation, in and out bend, and offsets for each tooth. This enables an unadjusted arch wire to perform variant alignment functions (i.e., with no further wire bending). In some examples, a series of clear molds may be used to produce teeth alignment. Orthodontic treatments generally last for two to three years.

SUMMARY

In a general aspect, an apparatus includes an orthodontic arch wire having a shape that corresponds to a dental arch, the arch wire having a first end portion that has a first series of grooves.

In another general aspect, an apparatus includes an orthodontic arch wire having a shape that corresponds to a dental arch, the arch wire having a first end portion that has a first series of grooves and a second series of grooves, and the first and second series of grooves are positioned on opposite sides of the first end portion.

In another general aspect, a method for orthodontic treatment is provided. The method includes providing an orthodontic arch wire having a shape that corresponds to a dental arch, the arch wire having a first end portion that has a first series of grooves; and using a first gear to engage the first series of grooves to provide a first longitudinal force to the arch wire.

In another general aspect, a method for orthodontic treatment is provided. The method includes attaching a first orthodontic bracket to a first tooth, the first orthodontic bracket having a first gear and a second gear; providing an orthodontic arch wire having a shape that corresponds to a dental arch, the arch wire having a first end portion that has a first series of grooves and a second series of grooves, the first and second series of grooves being positioned on opposite sides of the first end portion; and using the first and second gears to engage the first and second series of grooves, respectively, to provide a first longitudinal force to the arch wire.

Other aspects include other combinations of the features recited above and other features, expressed as methods, apparatus, systems, program products, and in other ways. Advantages of the aspects and implementations may include one or more of the following. The orthodontic brackets can be active brackets or smart brackets. A remote orthodontic system can allow active brackets or smart brackets to be remotely controlled or adjusted. The active brackets can generate force, and the force applied to the teeth can be increased or decreased while the patient is at home. The progress of teeth alignment can be monitored remotely. The remote orthodontic system can provide feedback and report symptoms, if any, to the orthodontist. In cases where adjustments to the original treatment plans are needed, the force adjustments can be made and applied while the patient is at home without the need to visit the dental clinic. The system can also provide an estimate of the remaining treatment time based on current progress of treatment. The system can reduce the trial and error in orthodontic treatment by using proper biomechanical pre-planning and insistent re-adjustment and monitoring. The system can improve the accessibility for orthodontic treatment in rural areas, and may reduce the number of days that school children miss classes. The orthodontic treatment outcomes may be more predictable, leading to a better quality with potentially reduced treatment side effects.

DESCRIPTION OF DRAWINGS

Like reference symbols in the various drawings indicate like elements.

DETAILED DESCRIPTION

This document describes an orthodontic system that enables an orthodontist to remotely monitor orthodontic braces on patients and make adjustments when necessary in a precise and predictable manner. In some implementations of the remote orthodontic system, the orthodontic system includes smart brackets in which each bracket has a miniature motor that drives a miniature gear, which in turn drives small rods or posts that push against an arch wire, generating a reaction force that pushes against the bracket's wings, in which the reaction force is transferred to the corresponding tooth to provide the required force for alignment of the tooth. The number of miniature motors and the configuration of the motor(s) can vary depending on design and functions. For example, the orthodontic system can include smart brackets in which each bracket has two miniature motors that drive miniature gears, which in turn pull or push an arch wire to generate opposing forces for alignment of the corresponding tooth (by generating couple forces system). In other implementations of the remote orthodontic system, the orthodontic system includes smart brackets in which each bracket has one or more miniature motors that drive one or more miniature gears, which in turn drive a rotatable base to provide root torque to the bracket for generating a force for alignment of the corresponding tooth. In some implementations of the remote orthodontic system, the orthodontic braces include arch wire segments connected by smart brackets in which each bracket has one or more miniature motors that apply forces to the arch wire segments, such that the combination of the forces generated by the plurality of brackets provide the proper amount of force for the alignment of each individual tooth.

Figure 1:
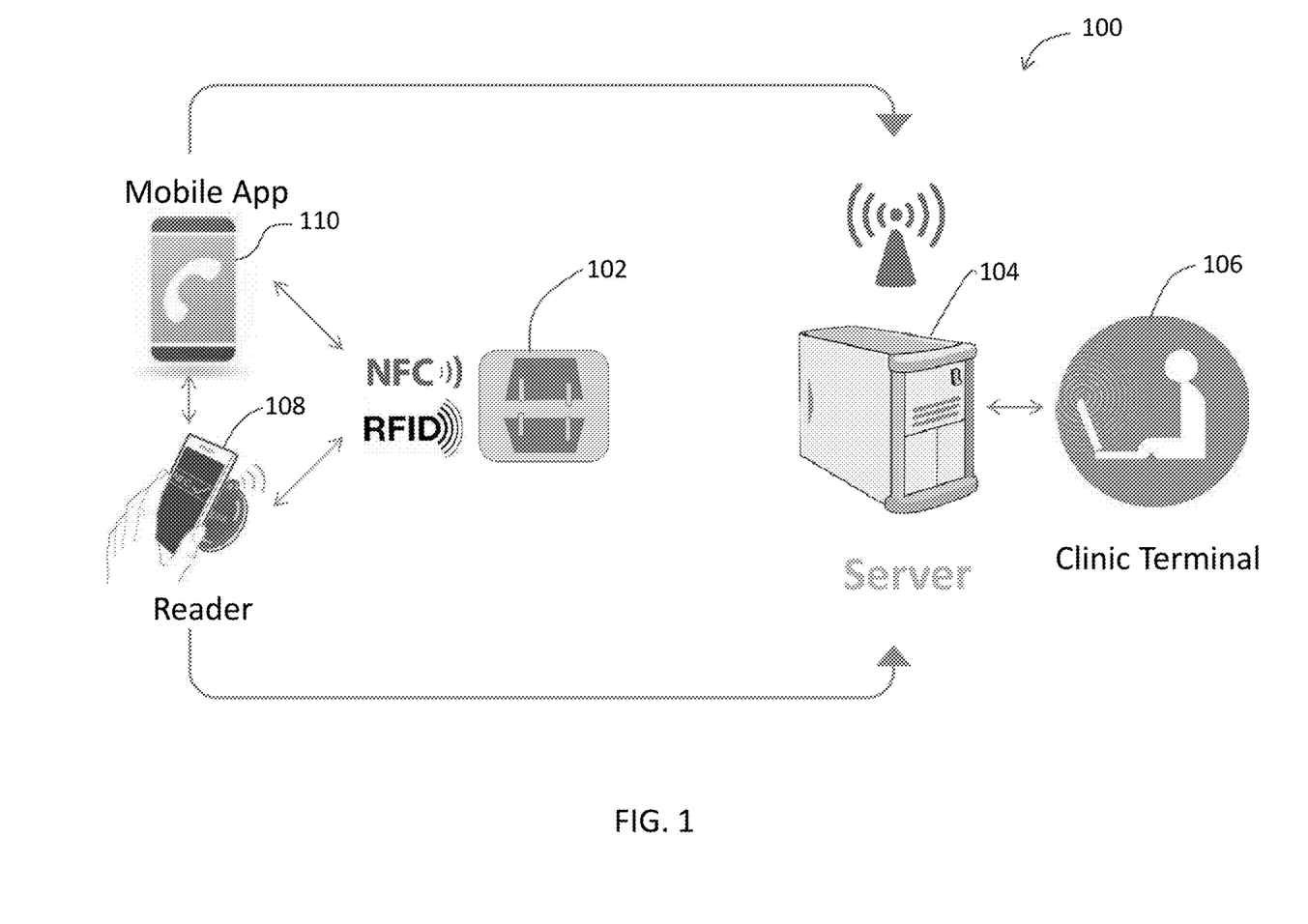
FIG. 1 is a diagram of an exemplary remote orthodontic system.

Referring to FIG. 1, a remote orthodontic system 100 includes orthodontic braces composed of smart brackets 102 (only one is shown in the figure) that communicate wirelessly with a computer server 104. The computer server 104 can be a physical machine located at the patient's home, or it can be a virtual server commonly referred to as a cloud server that resides remotely. The following describes examples in which the computer server 104 is a cloud server. In some examples, the computer server 104 may interact wirelessly with the brackets 102 by receiving signals from or sending signals to the brackets 102. This interaction occurs through, e.g., a home-based reader 108 or a user's cell phone 110, while the computer server 104 communicates with a clinic terminal 106 at a dental clinic. The computer server 104 receives signals from the brackets 102 (e.g., through the reader 108 or the cell phone 110), determines the current configurations of the brackets 102, determines whether adjustments are necessary, and sends back signals using the same route (e.g., through the reader 108 or the cell phone 110) to the brackets 102 in order to control motors in the brackets 102 to make the necessary adjustments. The computer server 104 communicates with the terminal 106 at the dental clinic to enable an orthodontist and/or other healthcare providers to monitor the configurations of the brackets 102 and enter commands to make additional adjustments when necessary.

In some implementations, when the patient first visits the orthodontist, the orthodontist may prescribe a treatment plan that specifies the amount and direction of force to be applied to each tooth at different time periods. The orthodontist may provide an electronic file that includes the treatment plan, and the patient may download, from the computer server 104, the electronic file having updated data containing the treatment plan to the reader 108 or the cell phone 110. The reader 108 or the cell phone 100 may execute an orthodontic application program that uses the information about the treatment plan to interact with the brackets 102.

After the first visit to the orthodontist, and at each follow up visit every three or four weeks, the orthodontist executes the orthodontic treatment program on the server 104. The orthodontic treatment program may analyze signals received from the brackets 102 to determine the progress of teeth alignment. The program may compare the current progress with the prescribed treatment plan and determine which brackets need to be adjusted to increase or decrease the force applied and its direction to the corresponding tooth, or to adjust the torque applied by the bracket to the tooth. The program instructs the server 104 to send signals to the brackets 102 to configure the brackets 102 such that each tooth receives the proper amount of force metrics according to the prescribed treatment plan.

Because the adjustments to the brackets 102 can be conveniently performed at the patient's home, the treatment plan may have instructions for more frequent bracket adjustments at finer time intervals, such as twice every month. The patient has the option of making adjustments to the brackets at times that are convenient to the patient.

The wireless reader 108 can interact wirelessly with the brackets 102 using a communication protocol similar to, e.g., the RFID protocol, Bluetooth protocol, or other protocols. The wireless reader 108 may be connected to the computer server 104 through a wire connection or a wireless link. The mobile phone 110 executing the orthodontic application program may interact wirelessly with the brackets 102 using a communication protocol similar to, e.g., the near-field communication protocol, Bluetooth protocol, or other protocols. The system may operate in, e.g., the 401-406 MHz, 902-928 MHz, 2400-2483.5 MHz, and/or 5725-5850 MHz bands. The mobile phone 110 may communicate with the computer server 104 through a wireless link.

In some implementations, the smart bracket 102 has sensors that can detect the amount of force (and/or the position trajectories) being applied to the tooth through the arch wire. Alternatively the sensors can be attached to or embedded in the arch wire itself. The sensors provide feedback signals so that the orthodontic treatment program executing on the computer server 104 can determine that the correct amount of force and the direction of force are applied to each tooth to ensure its proper alignment and positioning. If, after configuring the brackets 102, the sensors determine that the force/direction applied to the tooth deviates from the prescribed amount by more than a threshold value, the program may generate an alert signal, indicating that the patient should contact the orthodontist. Alternatively, the program can readjust and apply the new biomechanical force specifications. Upon receiving an instruction from the patient, the computer server 104 may send the data from the sensor to the clinic terminal 106 so that the orthodontist may determine whether it is possible to reconfigure the brackets remotely, or to inform the patient that it is necessary to return to the dental clinic for further examination and adjustment.

Figure 2:
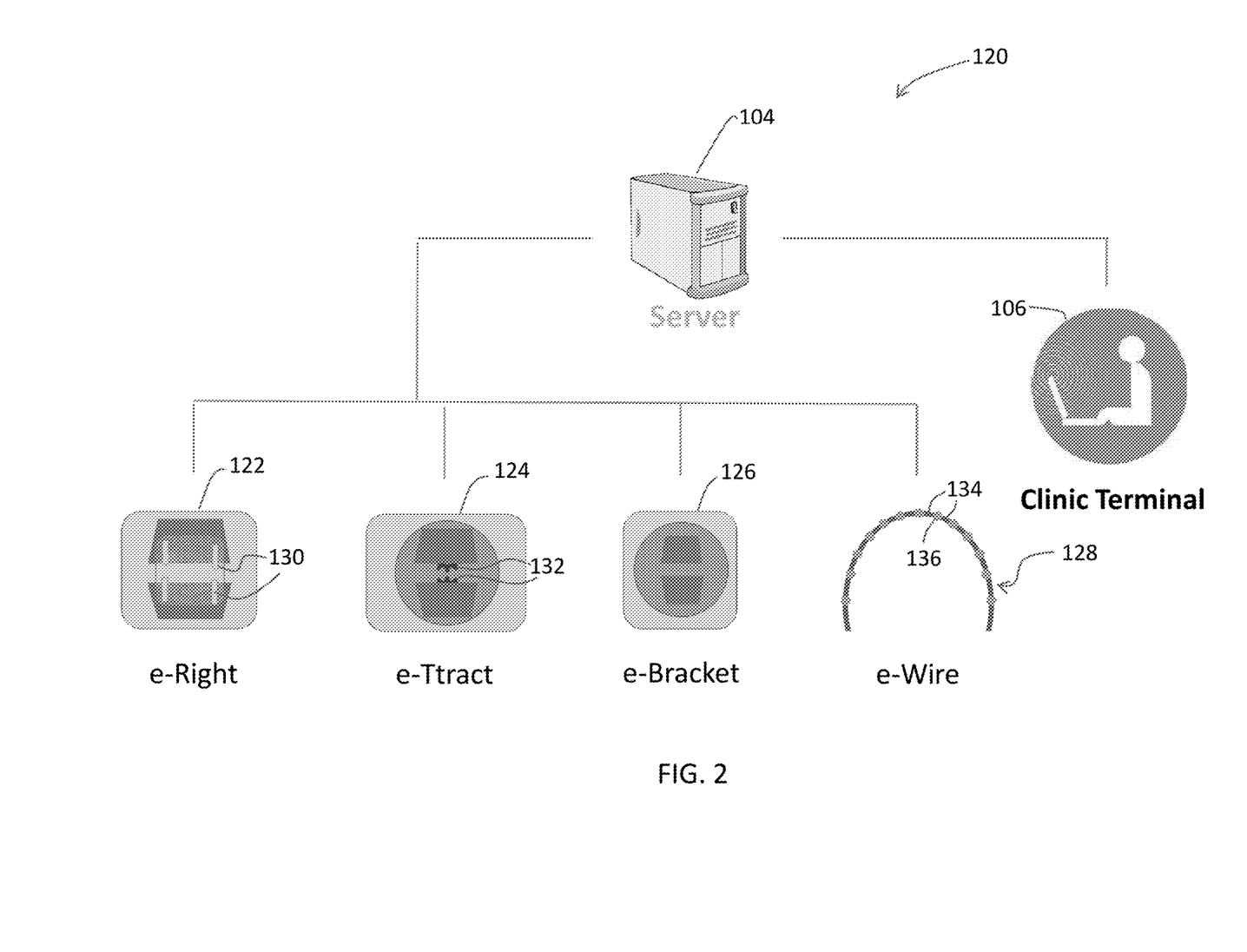
FIG. 2 is a diagram of various modules of the remote orthodontic system.

Referring to FIG. 2, a remote orthodontics system 120 may include a server 104 that communicates with different types of smart orthodontic braces, or orthodontic braces that include more than one type of smart brackets (individually or as a group). The computer server 104 may execute an orthodontic treatment program that is configured to control the various types of braces having various types of smart brackets. The server 104 may communicate with a clinic terminal 106 to enable an orthodontist to remotely monitor treatment progress or provide adjustments.

For example, one type of smart bracket is bracket 122, referred to as the e-Right bracket. The e-Right bracket 122 includes miniature motors that drive miniature gears, which in turn drive small rods 130 that push against an arch wire inserted into a slot of a bracket attached to a tooth. The small rods 130 provide forces that in combination produce the desired amount of force in the desired direction that is applied to the corresponding tooth to provide the required movement for alignment of the tooth.

A second type of smart bracket is bracket 124, referred to as the e-Tract bracket. The e-Tract bracket has two miniature motors that drive miniature gears 132, which in turn pull or push an arch wire (inserted in between) to generate retracting or protracting forces for movement and/or alignment of the corresponding tooth (or a group of teeth).

A third type of smart bracket is bracket 126, referred to as the e-Bracket in this document. The e-Bracket has one or more miniature motors that drive one or more miniature gears, which in turn drive a rotatable base to provide torque to the bracket 126 for generating a force for alignment of the corresponding tooth.

A fourth type of orthodontic braces variation is e-Wire braces 128. The e-Wire braces 128 include arch wire segments 134 connected to smart brackets 136 in which each bracket 136 has one or more miniature motors that apply forces to the arch wire segments 134, such that the interaction of the brackets 136 and wire segments 134 result in the proper amount of forces being applied to the teeth that need adjustment. Each arch wire segment is attached to the corresponding tooth surface in order to translate the delivered force. A patient may use any configuration of two or more of the e-Right bracket 122, e-Tract bracket 124, e-Bracket 126, or e-Wire braces 128 at the same time. The following describes details of the tract arch wires that can be used with e-Tract brackets 124.

Figure 3:
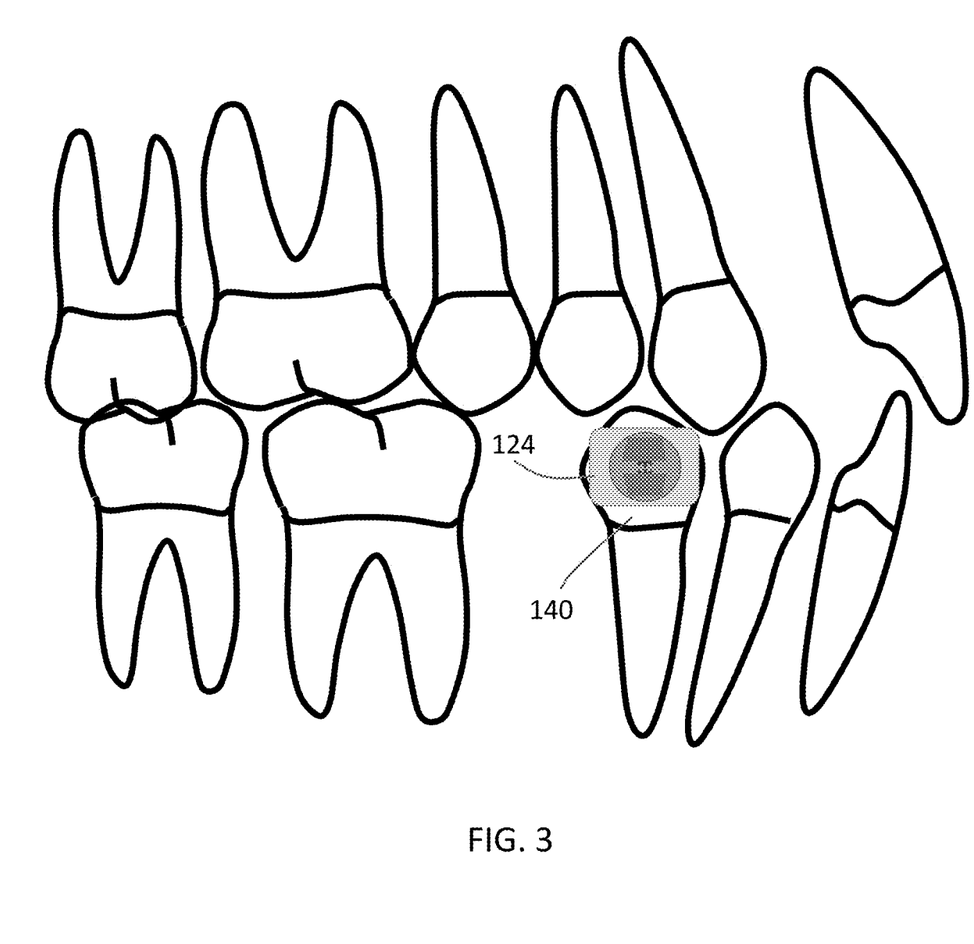
FIG. 3 is a diagram of an e-Tract bracket attached to a tooth.

Referring to FIG. 3, an e-Tract bracket 124 may be attached to a tooth 140 (in this example, a molar tooth) and provide a force for moving the tooth. This is useful for "protracting" or "retracting" of the anterior teeth. The e-Track bracket 124 can be used with a tract arch wire (not shown in FIG. 3), which will be described below.

Figure 4A:
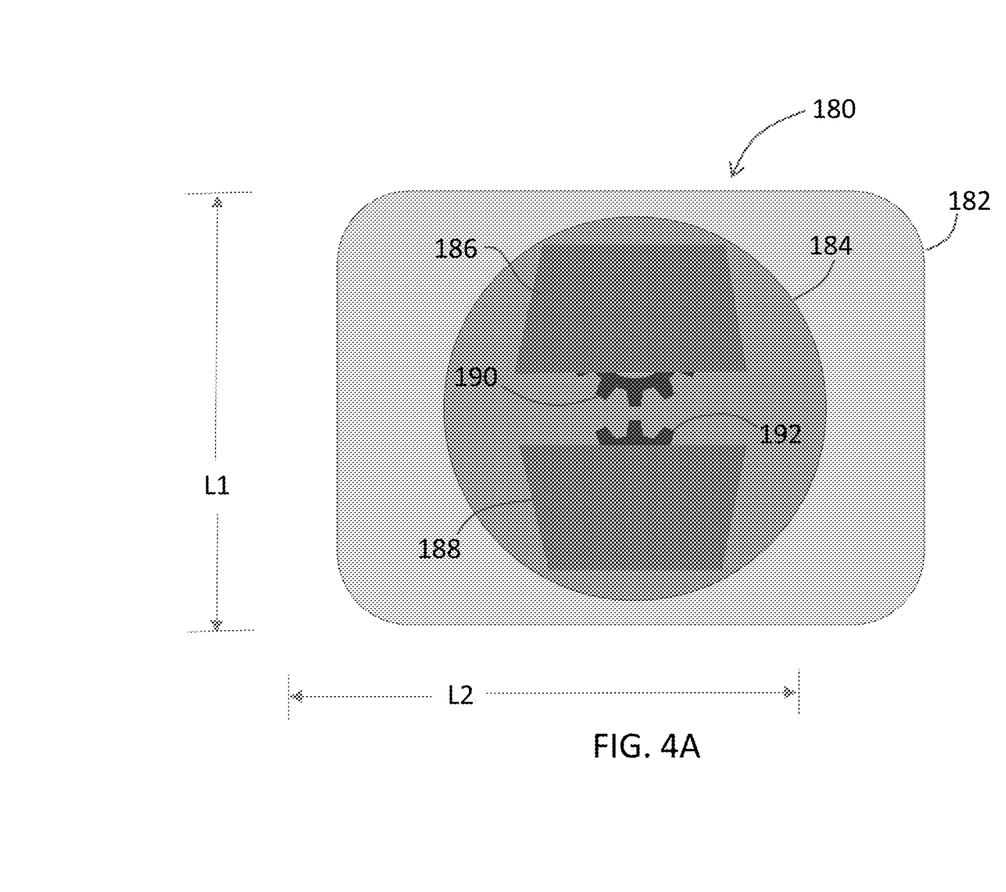
FIGS. 4A, and 4B, 5, 6A, and 6B are diagrams of exemplary e-Tract brackets.
Figure 4B:
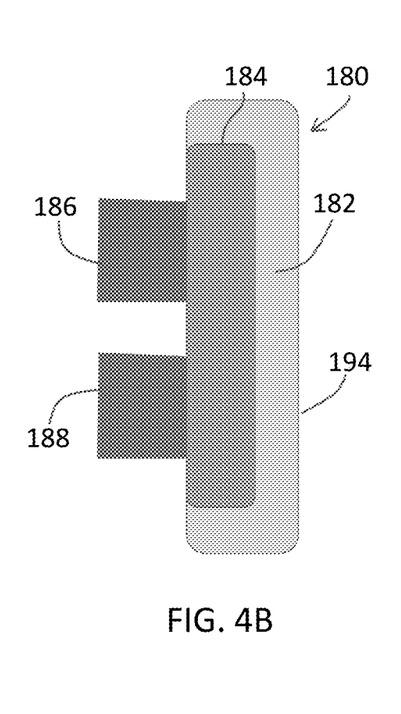

Referring to FIGS. 4A and 4B, in some implementations, an e-Tract bracket 180 can be used as an auxiliary tool with the existing orthodontic bracket system, or in combination with new brackets. The e-Tract bracket 180 can generate retraction or protraction forces through simultaneous rotating gear action coupled with an inter-locking serrated arch wire. The type of traction would depend on the gears' rotation direction. The e-Tract bracket 180 can be used in combination with other brackets to provide a bracing function to facilitate the overall alignment. FIG. 4A shows a front view of the bracket 180 while FIG. 4B shows a side view of the bracket 180. Gears on the bracket 180 can lock onto notches on a specially designed arch wire to generate a retraction or protraction force on the arch wire. The e-Tract bracket 180 can have, e.g., a height L1 of about 5 mm and a length L2 of about 11 mm. The dimensions of the e-Tract bracket 180 can vary depending on the amount of force required and the size of the tooth on which the bracket 180 is attached.

The bracket 180 includes a base 182, a support 184, an upper member 186, and a lower member 188. In some examples, a back surface 194 of the base 182 attaches to a molar (last) tooth. In some examples, the base 182 is fitted on a mini-screw supporting implant. The upper member 186 houses a miniature motor and a miniature gear 190. The miniature motor in the upper member 186 drives the miniature gear 190. The lower member 188 houses a miniature motor and a miniature gear 192. The miniature motor in the lower member 188 drives the miniature gear 192.

Figure 5:
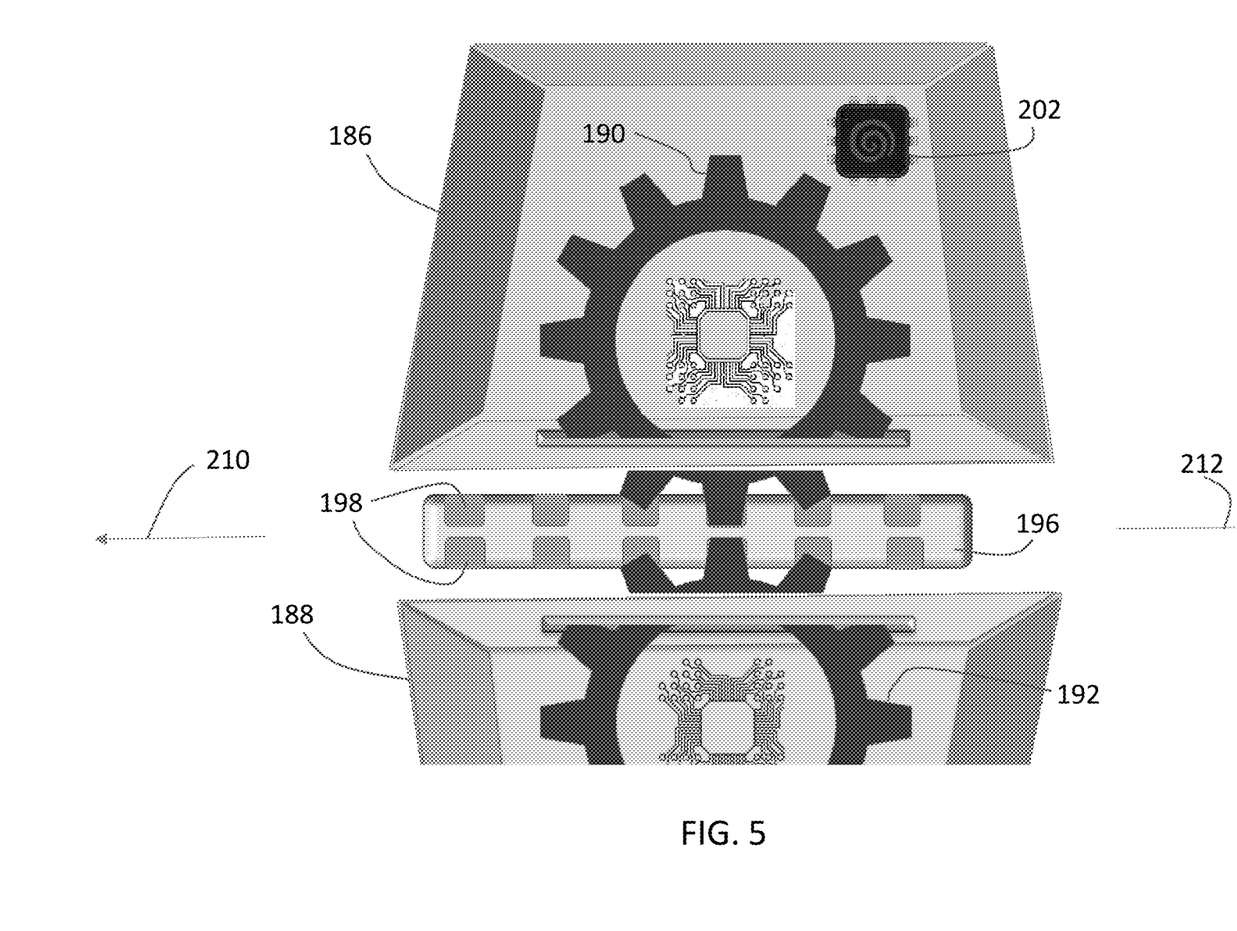

Referring to FIG. 5, when the upper gear 190 rotates in a clockwise direction and the lower gear 192 rotates in a counterclockwise direction, the teeth of the gears 190, 192 engage notches 198 in the arch wire 196 and pulls the arch wire 196 in a direction 210 towards the left (when viewed from a direction facing the front side of the bracket 180). Conversely, when the upper gear 190 rotates in a counterclockwise direction and the lower gear 192 rotates in a clockwise direction, the teeth of the gears 190, 192 engage the notches 198 in the arch wire 196 and pulls the arch wire 196 in a direction 212 towards the right. The arch wire 196 can be coupled to other brackets so that the pulling (or pushing) force generated by the gears 190, 192 can be used to generate a force that is applied to the other brackets and the teeth to which the brackets are attached. The upper member 186 includes an integrated circuit chip 202 that has circuitry for controlling the miniature motor in the upper member 186. The lower member 188 also includes an integrated circuit chip that has circuitry for controlling the miniature motor in the lower member 188. In some implementations, a single chip controls the operations of the motors in the upper and lower members 186, 188. The chip can also be placed in the base 182. The integrated circuit chip 202 in the upper member 186 and the integrated circuit chip 202 in the lower member 188 can communicate wirelessly to external devices, such as the reader 108 or the cell phone 110.

Figure 6A:
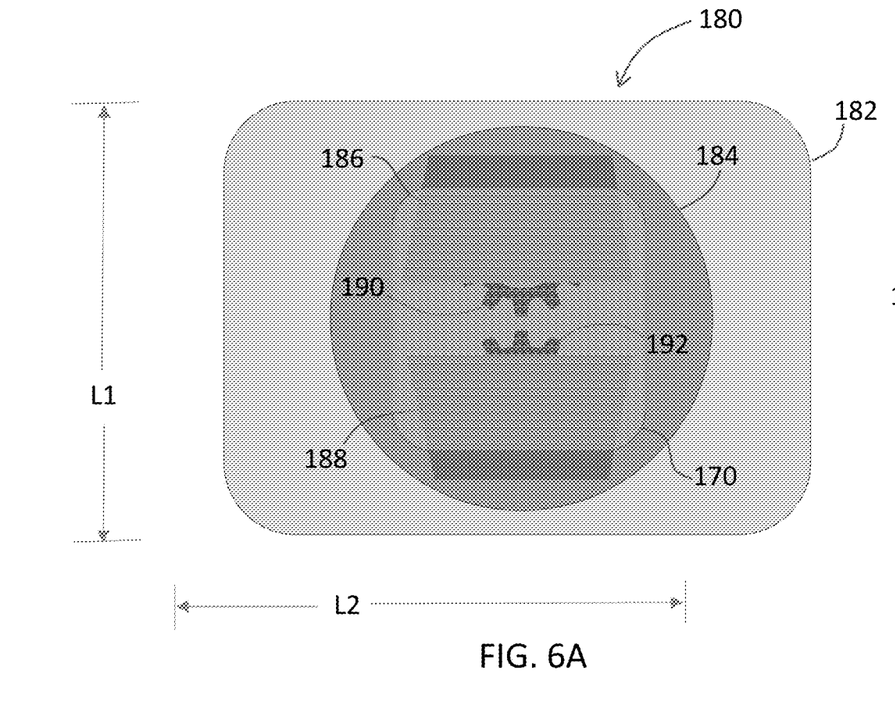
Figure 6B:
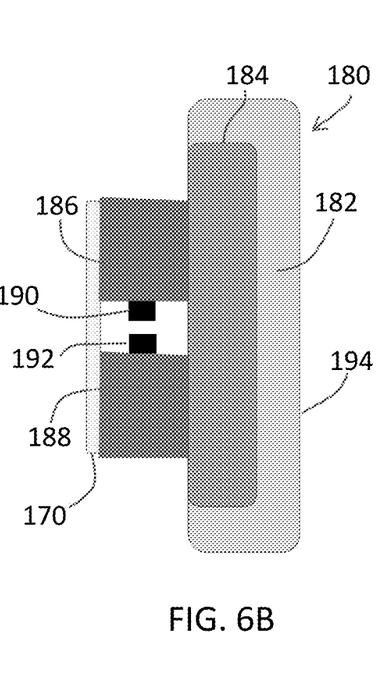

Referring to FIGS. 6A and 6B, in some implementations, the e-Tract bracket 180 can have a fixed or removable cover 170 that is used to ligate the arch wire 196 with the bracket slot.

In some implementations, the gears 190 and 192 can be driven manually. For example, a first miniature screw can be provided in the upper member 186, in which the thread of the screw engages the gear 190. The head of the first miniature screw can protrude outside of the upper member 186 so that the dentist or the patient can turn the first miniature screw to rotate the gear 190. Similarly, a second miniature screw can be provided in the lower member 188, in which the thread of the screw engages the gear 192. The head of the second miniature screw can protrude outside of the lower member 188 so that the dentist or the patient can turn the second miniature screw to rotate the gear 192. As the gear 190 and/or 192 are rotated, the arch wire 196 is pushed or pulled accordingly. In some implementations, the upper gear 190 can be manually driven, where the lower gear 192 simultaneously follows the action of the upper gear 190. Alternatively, the gear 190 can be joined with the gear 192 via, e.g., a cord, through the bracket support structure 184, to allow for a simultaneous coupled gear action. Additionally, the gear 190 (and/or 192), has a locking mechanism to prevent counter rotation after activation on a certain direction.

Figure 7:
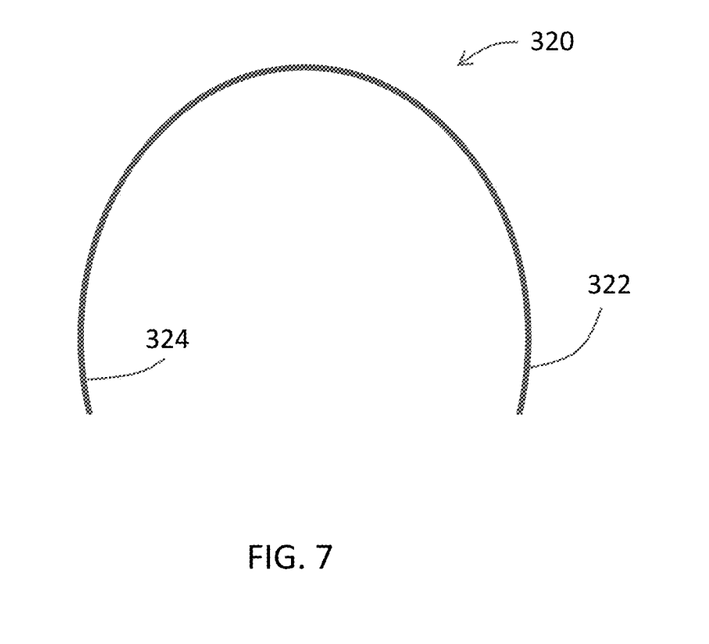
FIGS. 7 to 10 are diagrams of tract arch wires.
Figure 8:
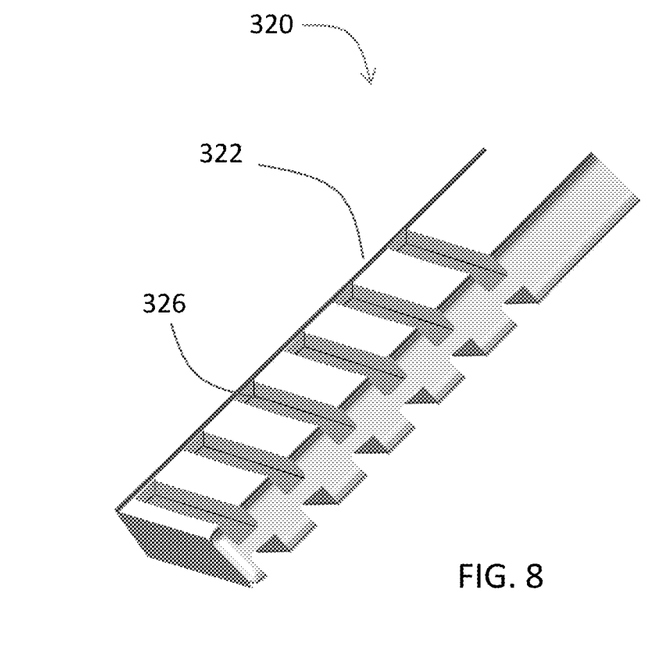

Referring to FIGS. 7 and 8, in some implementations, a tract arch wire 320 has a shape that is similar to a dental arch. Each end portion (322, 324) of the tract arch wire 320 has grooves or notches 326 that can be driven by gears. For example, a third of the arch wire 320 near one end can have grooves 326, and a third of the arch wire 320 near the other end can have grooves 326. The tract arch wire 320 can be used in combination with the e-Tract bracket 180 (FIG. 4A). The tract arch wire 320 of FIGS. 7 and 8 can be the arch wire 196 of FIG. 5. For example, the tract arch wire 320 can be made of stainless steel alloy. For example, the arch wire 320 can be constructed to have a rectangular or round cross-sectional shape, with a width or diameter, respectively, ranging from, e.g., 0.016 inch by 0.022 inch to 0.021 inch by 0.027 inch ("full slot size"). The arch wire 320 can also have a round cross-sectional shape. The arch wire 320 allows for "protracting" or "retracting" of the anterior teeth, hence the name "tract" arch wire.

Figure 9:
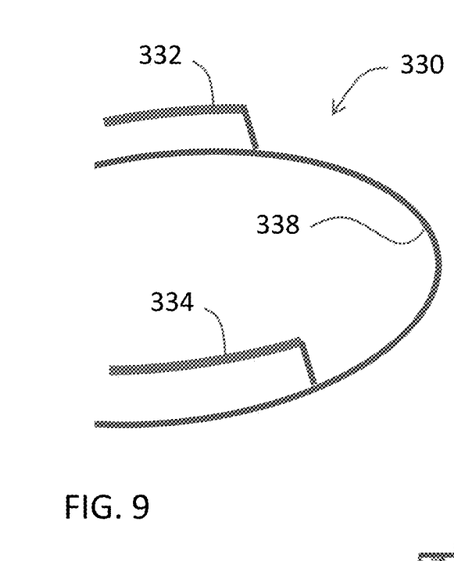
Figure 10:
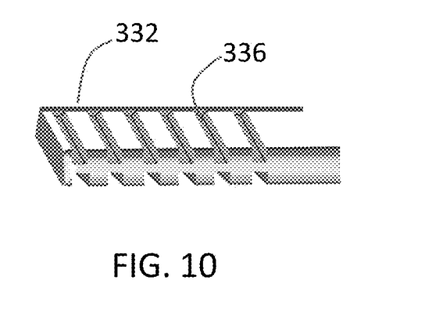

Referring to FIGS. 9 and 10, in some implementations, a tract arch wire 330 has a main wire 338 and two branch wires 332 and 334. The main wire 338 is smooth and does not have any notch, whereas each of the branches 332 and 334 has notches 336 that can be pulled or pushed by gears. In this configuration, the tract arch wire 330 can be used with e-Tract brackets 180 that are mounted on mini-screw supporting implants placed gingivally to the teeth crown.

Figure 11:
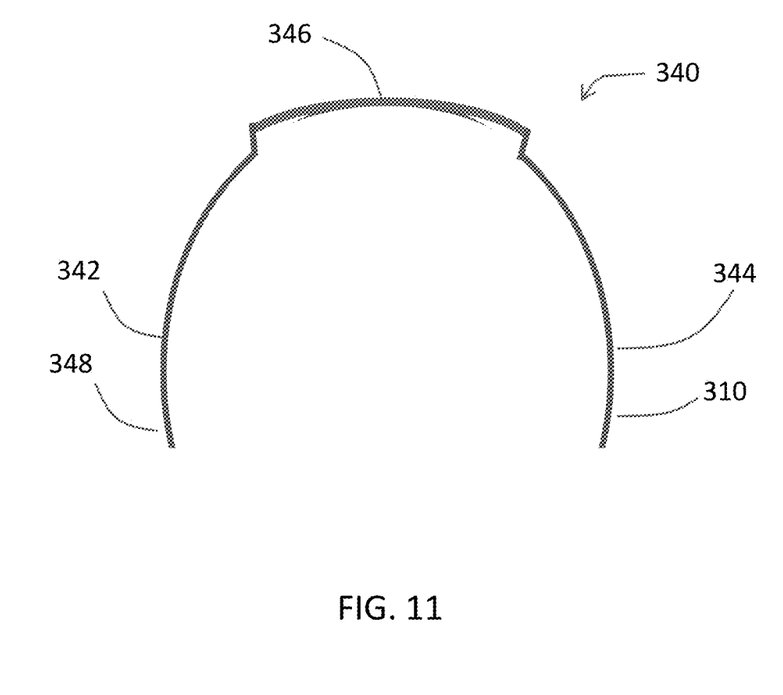
FIG. 11 is a diagram of a compensating arch wire.

Referring to FIG. 11, because the smart brackets, such as the e-Right bracket 122 (FIG. 2) and the e-Bracket 220 (FIG. 2), may be slightly thicker than conventional orthodontic brackets, it is useful to have a compensating arch wire 340 in which a portion 346 of the arch wire is offset from the rest of the arch wire. For example, the distance between the portion 346 of the arch wire to adjacent teeth is larger than the distance between a portion 342 or 344 of the arch wire to adjacent teeth. In some examples, the portion 346 of the arch wire coupled to smart brackets can be made of a material that is different from the other portions of the arch wire that are coupled to conventional brackets. In the example of FIG. 11, the smart brackets are used for anterior teeth. For example, a portion 348 near one end can have grooves 326, and a portion 310 near the other end can have grooves 326. The grooves 326 allow the use of e-Track brackets 124 to protract or retract the anterior teeth.

Figure 12:
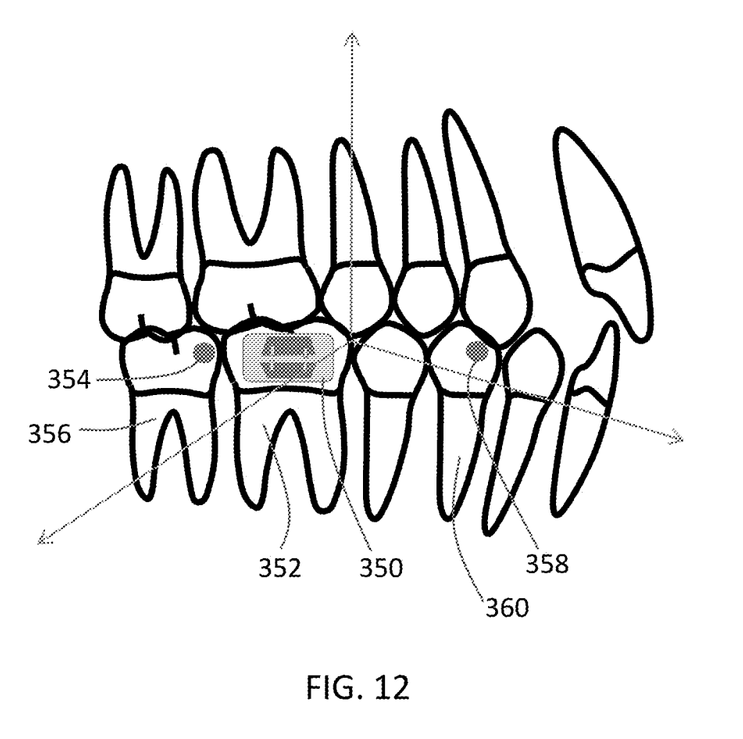
FIG. 12 is a diagram of a smart bracket and exemplary reference markers.

Various smart orthodontic brackets and wires have been described above. These smart brackets and wires can be used in the remote orthodontic system 100 of FIG. 1. Referring to FIG. 12, in order to monitor the movement of the tooth under treatment, markers can be attached to one or more adjacent teeth. For example, a bracket 350 is attached to a tooth 352 that needs to be aligned. The bracket 350 may engage a tract arch wire that is coupled to an e-Track bracket 124. A first marker 354 is attached to a tooth 356, and a second marker 358 is attached to another tooth 360. When the bracket 350 is first installed on the tooth 352, a set of one or more pictures of the teeth are taken. After a period of time, such as three or four weeks later, a second set of one or more pictures of the teeth are taken. The movement of the tooth 352 under treatment relative to the other teeth 356 and 360 can be measured by comparing the position of the bracket 350 relative to the markers 354 and 358 that function as reference points.

In some examples, the patient takes images of the teeth and sends them to the orthodontist, who monitors the progress of the treatment. If the movement of the tooth 352 is according to plan, then the e-Track bracket 124 and the bracket 350 will be adjusted according to plan. After adjustment, the e-Track bracket 124 will provide the appropriate forces to the tract arch wire 320, which in turn provides appropriate forces to the orthodontic brackets coupled to the trach arch wire 320. If the movement of the tooth 352 is outside of acceptable boundaries, then the orthodontist may adjust the treatment plan or ask the patient to return to the clinic for further examination and/or treatment. When the orthodontist needs to adjust the treatment plan, the orthodontist may send an instruction from the clinic terminal 106 to the server computer 104 to adjust the treatment plan stored locally at the server 104.

In some examples, the mobile phone 110 may execute an orthodontic app that provides instructions to the patient or a helper of the patient on how to take pictures in order to accurately determine the movement of the tooth 352. For example, a helper may use the camera on the mobile phone 110 to take pictures of the patient's teeth. A reference image that was previously taken can be overlaid on a live view taken by the phone camera. The reference image may show the two markers 354 and 358, so that the helper may position and orient the camera to take a picture of the teeth in which the markers 354 and 358 are at similar positions in the new picture. This makes it easier to compare the current picture with a previously taken picture to determine the movement of the tooth 352. A set of orthodontic biomechanical algorithms can be used by the system 100 to determine the auto adjustments to be made to the smart brackets, such as increasing or decreasing the forces applied by the e-Tract bracket 124 to the tract arch wire segments.

The e-Tract brackets 124 used with the tract arch wire 320 may have sensors for sensing the force applied to the corresponding tooth. For example, a microelectromechanical sensor system having piezoresistive microsensors attached between the smart bracket and the tooth can be used to take measurements that can be used to calculate forces applied to the tooth in the x, y, and z directions, and moments in the x, y, and z directions. By monitoring the forces actually applied to the tooth, the system 100 can determine whether the motors in the smart brackets need to be adjusted to apply more or less force in a certain direction.

The chip 202 (FIG. 5), the miniature motors, and the sensors system can be powered wirelessly by beaming power to microcoils in the smart nodes. The chip 202 may include circuitry for modulating data sent to the reader 108 or the server 104, or demodulating the signals sent from the reader 108 or the server 104.

The remote orthodontic system 100 helps orthodontists and their patients to have a high quality orthodontic treatment, with reduced visits to the dental office and reduced costs. For example, the adjustments to the smart brackets and arch wires can be made while the patients are at home. The orthodontists can also monitor the treatments and make adjustments to the treatment plans from home, allowing more flexible work schedules.

A novel tract arch wire that can be used with smart orthodontic brackets that can generate and deliver forces has been described above. The system 100 is interactive in which the patient and the treatment provider are able to monitor the status of teeth alignment and report responses and symptoms. The system can be remotely controlled, enabling quick re-adjustment and auto-correction. The system can apply biomechanical equations based on the known static and dynamic equilibrium laws and algorithms. The system provides treatments with predictable and improved outcomes, so the treatment duration can be accurately forecasted and better controlled.

Each of the computer server 104, mobile phone 110, and reader 108 can include one or more processors and one or more computer-readable mediums (e.g., RAM, ROM, SDRAM, hard disk, optical disk, and flash memory). The one or more processors can perform various calculations or control functions described above. The calculations and various functions can also be implemented using application-specific integrated circuits (ASICs). The term "computer-readable medium" refers to a medium that participates in providing instructions to a processor for execution, including without limitation, non-volatile media (e.g., optical or magnetic disks), and volatile media (e.g., DRAM) and transmission media. Transmission media includes, without limitation, coaxial cables, copper wire and fiber optics.

The features described above can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., C, Java), including compiled or interpreted languages, and it can be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory (ROM) or a random access memory (RAM) or both. The essential elements of a computer are a processor for executing instructions and one or more memories for storing instructions and data. Generally, a computer will also include, or be operatively coupled to communicate with, one or more mass storage devices for storing data files. The mass storage devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM, CD-R, DVD-ROM, DVD-R, Blu-ray DVD disks. The processor and the memory can be supplemented by, or incorporated in, ASICs (application-specific integrated circuits). The chip 202 (FIG. 5) may include one or more processors described above. The chip 202 may also include one or more volatile or non-volatile memories for storing instructions to be executed by the one or more processors.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

Other embodiments are within the scope of the following claims. For example, a combination of various types of smart brackets can be used for treating one patient. The smart brackets and arch wires can be made of materials different from those described above. In some implementations, each smart bracket can include a radio frequency identification tag associated with a unique identifier. In some implementations, each chip (e.g., 202) has a unique identifier. This way, if a patient has multiple smart bracket, the server 104 can uniquely identify each smart bracket and send different instructions to different smart brackets.

What is claimed is:

1. An orthodontic apparatus comprising:
   an orthodontic arch wire having a shape that corresponds to a dental arch, the arch wire having a main wire and a first branch wire, in which the main wire has a first end and a second end, the first branch wire includes a first end portion that has a first series of grooves and a second series of grooves, the first series of grooves are positioned on a first side of the first end portion, the second series of grooves are positioned on a second side of the first end portion, and the first side and the second side are on opposite sides of the first end portion relative to each other,
   wherein the first branch wire is attached to the main wire at a first location of the main wire that is between the first end and the second end of the main wire, and both the main wire and the first branch wire are configured to extend from the first location toward a posterior direction.

2. The apparatus of claim 1, comprising a bracket having a first gear and a second gear, in which the first gear is configured to engage the first series of grooves and the second gear is configured to engage the second series of grooves, enabling one or both of the first and second gears to drive the first end portion and provide a force along a longitudinal direction of the arch wire.

3. The apparatus of claim 2 in which the first gear has teeth, and each tooth has a dimension that matches the dimension of each of the first series of grooves, enabling the first gear to drive the first end portion and provide the force or a portion of the force along the longitudinal direction of the arch wire.

4. The apparatus of claim 1 in which the orthodontic arch wire has a second branch wire, and the second branch wire has a second end portion that has a third series of grooves.

5. The apparatus of claim 1, comprising an orthodontic bracket that includes a gear having teeth, in which each tooth has a dimension that matches the dimension of each of the grooves, enabling the gear to drive the first end portion and provide a force along a longitudinal direction of the arch wire.

6. The apparatus of claim 1 in which the arch wire is made of at least one of stainless steel or a metal alloy.

7. The apparatus of claim 6 in which the arch wire is made of a metal alloy that comprises at least two different metal materials.

8. The apparatus of claim 1 in which the arch wire has at least one of a rectangular or round cross-sectional shape.

9. The apparatus of claim 8 in which the arch wire has at least one of (i) a cross-sectional dimension in a range from 0.014 inch by 0.022 inch to 0.021 inch by 0.027 inch or (ii) a diameter in a range from 0.014 inch 0.027 inch.

10. The apparatus of claim 1 in which the arch wire has a second branch wire, and the second branch wire has an end portion that has a series of grooves, wherein the main wire and the second branch wire are connected at a second location that is anterior to the second end of the main wire, and both the main wire and the second branch wire are configured to extend from the second location toward a posterior direction.

11. The apparatus of claim 1 in which the main wire has a first section that is anterior relative to the first location and a second section that is posterior relative to the first location, and both the first branch wire and the second section of the main wire are configured to be inserted into arch wire slots of brackets that are posterior relative to the first location.

12. An apparatus comprising:
an orthodontic arch wire having a shape that corresponds to a dental arch, the arch wire having a main wire and a first branch wire, in which the first branch wire includes a first end portion that has a first series of grooves and a second series of grooves, the first series of grooves are positioned on a first side of the first end portion, the first side is configured to face a first direction, the second series of grooves are positioned on a second side of the first end portion, the second side is configured to face a second direction that is opposite to the first direction;
a first bracket having a first gear that is configured to engage the first series of grooves on the first branch wire and a second gear that is configured to engage the second series of grooves on the first branch wire;
a second bracket having an arch wire slot configured to receive the main wire;
wherein the first branch wire is attached to the main wire at a first location of the main wire that is anterior to both the first bracket and the second bracket.

13. The apparatus of claim 12 in which each groove has a depth greater than 0 and less than 0.1 inch, and a width greater than 0 and less than 0.3 inch.

14. A method comprising:
providing an orthodontic arch wire having a shape that corresponds to a dental arch, the arch wire having a main wire and a first branch wire, in which the main wire has a first end and a second end, the first branch wire includes a first end portion that has a first series of grooves and a second series of grooves, the first series of grooves are positioned on a first side of the first end portion, the second series of grooves are positioned on a second side of the first end portion, and the first side and the second side are on opposite sides of the first end portion relative to each other,
wherein the first branch wire is attached to the main wire at a first location of the main wire that is between the first end and the second end of the main wire, and both the main wire and the first branch wire are configured to extend from the first location toward a posterior direction;
engaging, using a first gear that is part of a first bracket, the first series of grooves of the first branch wire;
engaging, using a second gear that is part of the first bracket, the second series of grooves of the first branch wire, the first and second gears driving the first end portion of the first branch wire and providing a force along a longitudinal direction of the arch wire.

15. The method of claim 14 in which the first bracket is attached to a tooth.

16. The method of claim 14 in which the first bracket is attached to a posterior tooth.

17. The method of claim 14 in which providing the orthodontic arch wire comprises providing an arch wire having a second branch wire that has a second end portion that has a third series of grooves.

18. The method of claim 17, comprising using a third gear that is part of a second bracket to engage the third series of grooves to provide a second longitudinal force to the arch wire.

19. The method of claim 18 in which providing the first longitudinal force comprises providing a first longitudinal force that protracts or retracts a left anterior tooth towards a left posterior tooth.

20. The method of claim 19 in which providing the second longitudinal force comprises providing a second longitudinal force that protracts or retracts a right anterior tooth towards a right posterior tooth.

21. The method of claim 14 in which the main wire has a first section that is anterior relative to the first location and a second section that is posterior relative to the first location, and the method comprises
inserting the first branch wire into an arch wire slot of the first bracket positioned posterior to the first location, and
inserting the second section of the main wire into an arch wire slot of a second bracket positioned posterior to the first location.

22. The method of claim 14 in which the first bracket is attached to an implant placed gingivally to a tooth.

23. The method of claim 14 in which the first bracket is attached to an implant placed gingivally to a posterior tooth.

24. A method comprising:
attaching a first orthodontic bracket to a first tooth or an implant placed gingivally to the first tooth, the first orthodontic bracket having a first gear and a second gear;
providing an orthodontic arch wire having a shape that corresponds to a dental arch, the arch wire having a main wire and a first branch wire, in which the first branch wire includes a first end portion that has a first series of grooves and a second series of grooves, the first series of grooves are positioned on a first side of the first end portion, the second series of grooves are positioned on a second side of the first end portion, and the first side and the second side are on opposite sides of the first end portion relative to each other,
wherein the first branch wire is attached to the main wire at a first location of the main wire that is anterior to the first tooth; and
engaging, using the first and second gears, the first and second series of grooves, respectively, to provide a first longitudinal force to the arch wire.

25. The method of claim 24, comprising using the first longitudinal force to perform at least one of protract or retract an anterior tooth.

26. The method of claim 24 in which providing the orthodontic arch wire comprises providing an arch wire having a second branch wire that has a second end portion that has a third series of grooves and a fourth series of grooves, the third and fourth series of grooves being positioned on opposite sides of the second end portion.

27. The method of claim 26, comprising attaching a second orthodontic bracket to a second tooth or an implant placed gingivally to the second tooth, the second orthodontic bracket having a third gear and a fourth gear to engage the third and fourth series of grooves, respectively, to provide a second longitudinal force to the arch wire.

28. The method of claim 24 in which the first gear has teeth, each tooth of the first gear has a dimension that matches the dimension of each of the first series of grooves, the second gear has teeth, and each tooth of the second gear has a dimension that matches the dimension of each of the second series of grooves, enabling the first and second gears to drive the first end portion and provide the force along the longitudinal direction of the arch wire.

29. The method of claim 24 in which the main wire has a first section that is anterior relative to the first location and a second section that is posterior relative to the first location, and the method comprises
   inserting the first branch wire into an arch wire slot of the first orthodontic bracket in which the first orthodontic bracket is positioned posterior to the first location, and
   inserting the second section of the main wire into an arch wire slot of a second bracket positioned posterior to the first location.

* * * * *